(12) United States Patent
Tornier et al.

(10) Patent No.: US 6,599,295 B1
(45) Date of Patent: Jul. 29, 2003

(54) DEVICE FOR SETTING AND REMOVING AN IMPLANT SUCH AS A SUTURE ANCHOR

(75) Inventors: Alain Tornier, Saint Ismier (FR); Francois Bonnomet, Strasbourg (FR)

(73) Assignee: Tornier SA, Saint Ismier (FR)

( * ) Notice: Subject to any disclaimer, the term of this patent is extended or adjusted under 35 U.S.C. 154(b) by 0 days.

(21) Appl. No.: 09/673,892

(22) PCT Filed: Apr. 21, 1999

(86) PCT No.: PCT/FR99/00939

§ 371 (c)(1),
(2), (4) Date: Nov. 27, 2000

(87) PCT Pub. No.: WO99/53842

PCT Pub. Date: Oct. 28, 1999

(30) Foreign Application Priority Data

Apr. 21, 1998 (FR) .............................................. 98 05204

(51) Int. Cl.[7] .............................................. A61B 17/04
(52) U.S. Cl. .......................................... 606/104; 606/75
(58) Field of Search ........................ 606/104, 99, 139, 606/142, 144, 75; 623/13.14

(56) References Cited

U.S. PATENT DOCUMENTS

| | | | | |
|---|---|---|---|---|
| 4,367,746 A | * | 1/1983 | Derechinsky | 29/243.56 |
| 5,501,695 A | | 3/1996 | Anspach, Jr. et al. | 606/232 |
| 5,649,963 A | | 7/1997 | McDevitt | 606/232 |
| 5,749,899 A | * | 5/1998 | Bardin | 606/104 |
| 6,010,513 A | * | 1/2000 | Tormala et al. | 606/142 |

* cited by examiner

*Primary Examiner*—Kevin Shaver
*Assistant Examiner*—Melba Bumgarner
(74) *Attorney, Agent, or Firm*—Dowell & Dowell, PC

(57) ABSTRACT

A device for setting and removing a deformable implant from bone wherein the device includes a body on which is mounted a movable handle which is operatively connected to activating elements for displacing a rod relative to the body for deforming and/or removing an implant from the bone. The device further includes a rod locking and disengaging assembly which is movable from a first position to prevent movement of the rod to a second position to permit movement of the rod relative to the body.

24 Claims, 16 Drawing Sheets

DEVICE FOR SETTING AND REMOVING AN IMPLANT SUCH AS A SUTURE ANCHOR

BACKGROUND OF THE INVENTION

1. Field of the Invention

The present invention relates to a device, or instrument, for positioning or the withdrawal of an implant and, in particular, for a suture anchor for attaching soft tissues, such as ligaments or tendons, to bone to repair rotator cuffs and Bankart lesions.

2. Description of the Related Art

Patent EP 0 599 772 discloses a device allowing the positioning of a suture anchor in bone, which device is in the form of a gun. This gun, provided with a grip that can be manually operated, comprises a driving mechanism and a stop that activates the mechanism. The gun comprises a cylinder and a guide that contains a clip or a suture anchor designed to hold a suture thread. The gun ejects the clip, holding the suture thread, from the cylinder in order to anchor in the bone for various surgical interventions.

It must be noted that the removal of the suture anchors provided with deformable fixation means is effected by drilling a hole into the cortical bone; the diameter of such a hole is slightly greater than that of the fixation means. Under such conditions, the surgeon causes considerable damage to the cortical portion of the bone, preventing any possibility to remove or position a suture anchor.

The present invention has the particular aim to remedy these disadvantages.

SUMMARY OF THE INVENTION

The ancillary device of the present invention has as an object in particular the positioning or the removal of suture anchors of reversible expansion allowing the deformation of the expansion elements and the fastening of suture threads, or the deformation of the elements for fixation at the time of ligamentous or tendinous reinsertion operations under arthroscopies or on the surface.

The ancillary device for the positioning or the withdrawal of an elastically deformable implant into or from a bone of a patient according to the present invention includes a body onto which is affixed a mobile grip, tractive or activating elements that move a traction rod for the deformation of the implant, and a locking and disengaging device that allows the rod to move or not to move freely in a rotational and translational manner with respect to the body.

The positioning ancillary device according to the present invention also includes control means for the tractive force applied to the rod for the deformation of the implant.

The positioning ancillary device according to the present invention has a body that is provided with a first chamber that houses the tractive means or activating elements and a second chamber that houses the locking and disengaging device.

The tractive or activating means includes two plates between which is compressed a spring, and at least one of these plates interacts with a curved return mechanism actuated by the mobile grip to press the plate against the traction rod to have it return with respect to the body.

The locking and disengaging device is provided with a lever that is susceptible to be blocked by a catch elastically affixed to a fixed grip of the body. A plate is connected to a spring with adjustable tension so that the plate can press against the traction rod under a stress of the lever to pass from a disengaged vertical position to an engaged or locked tilted position.

The control means includes a nose affixed to the body in which is provided, around the rod that displaces freely, a plate affixed to a traction tube in which the rod slides.

The withdrawal ancillary device according to the present invention makes possible the opening of the fixation elements of the suture anchors inside of the spongy bone in order to remove them without having to bore a hole that would damage the surface of the cortical bone.

The withdrawal ancillary device according to the present invention includes a body to which is coupled a mobile grip, compression or activating means moving a compression rod for the deformation of the implant, and a locking or disengaging device that allows to have the compression rod move freely or not in a rotational and translational manner with respect to the body in order to adjust the travel of the rod.

The withdrawal ancillary device according to the present invention also includes anchoring means affixed to the body and rotating around the rod, that are designed to fasten inside of the implant to be removed.

The withdrawal ancillary device according to the invention includes a body provided with a first chamber in which are mounted the compression or activating means and a second chamber in which is housed the locking and disengaging device.

BRIEF DESCRIPTION OF THE DRAWINGS

The below description, taking into account the accompanying drawings, given as not limiting examples, allows a better understanding of the invention, of its characteristics and the advantages it may offer:

FIGS. 1 to 3 show an ancillary device 1 enabling, in particular, but not in a limiting manner the positioning of implants.

DESCRIPTION OF THE PREFERRED EMBODIMENT

Figure 1:
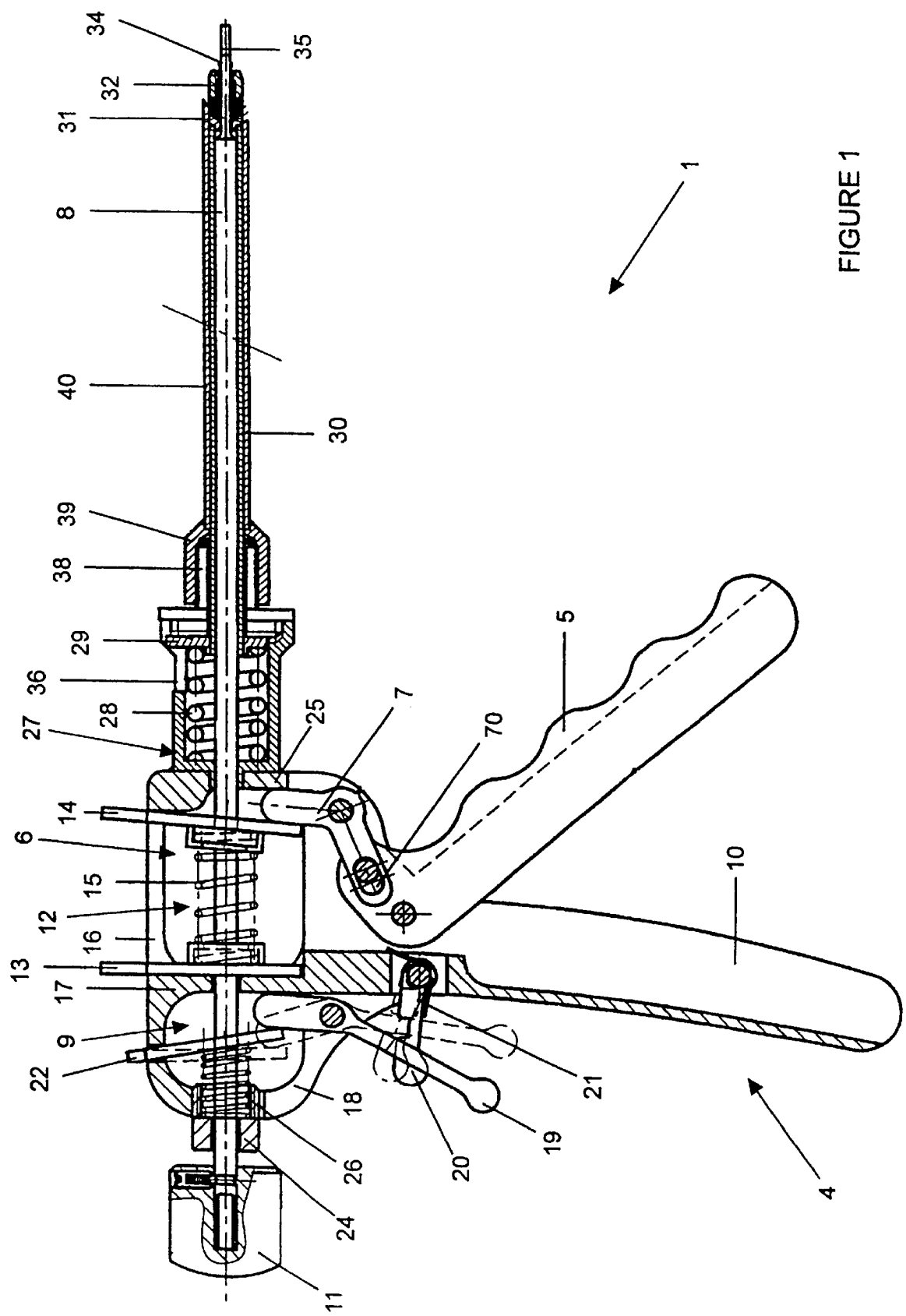
FIG. 1 is a sectional drawing illustrating the ancillary device according to the present invention.
Figure 2:
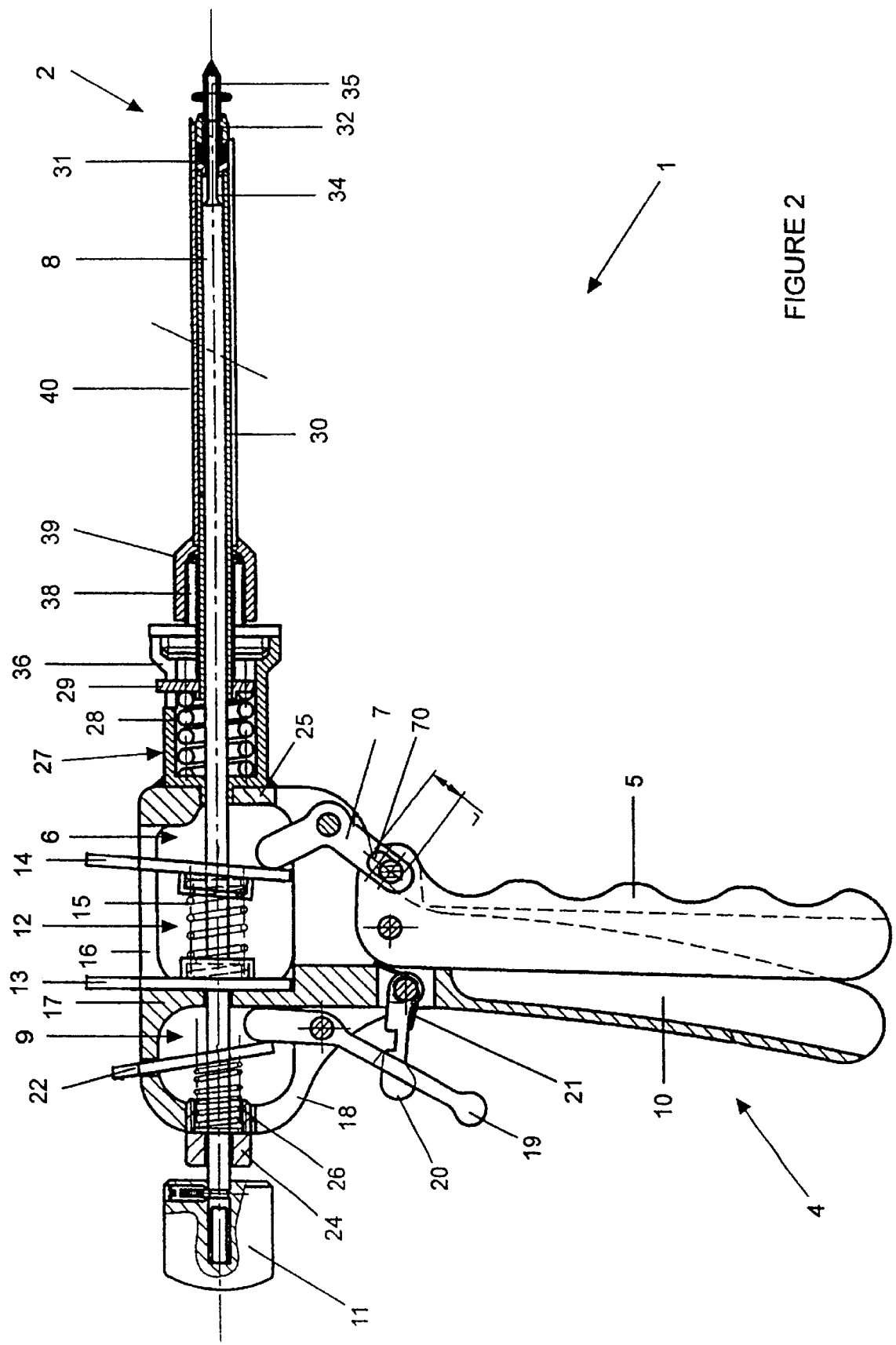
FIG. 2 is a sectional drawing illustrating the ancillary device in a position actuated for the deformation of the implant.
Figure 3:
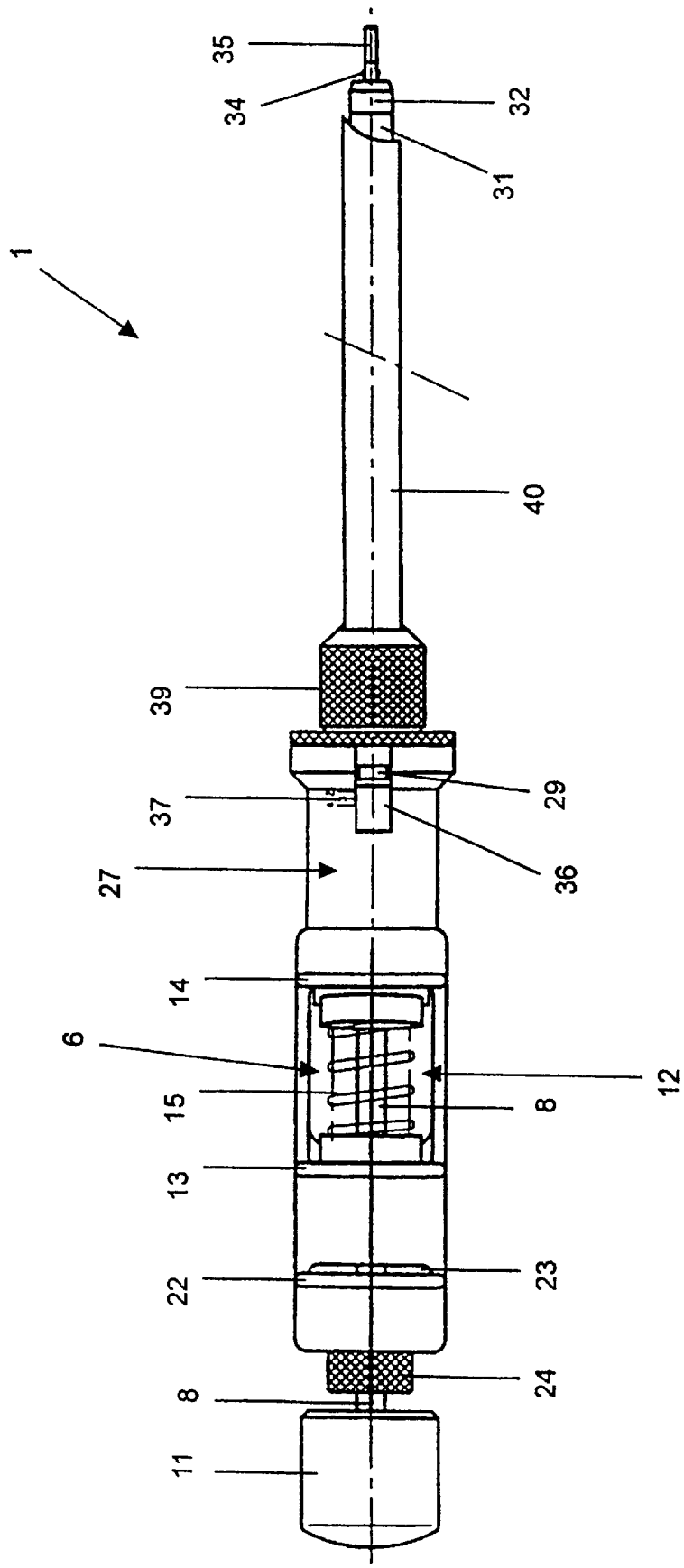
FIG. 3 is a horizontal projection illustrating the ancillary device according to the present invention.

The ancillary device 1 allows the positioning and fixation of reversible expansion suture anchors 2 and 3 in the bone of a patient.

The ancillary device 1 does also facilitate, at the moment of the fixation of the suture anchors 2 and 3 to the bone, the deformation of expansion elements, of fastening means for the suture treads or the deformation of the fixation elements of the anchor 3, at the time of the ligamentous or tendinous reinsertion effectuated by arthroscopy or open cut.

The ancillary device 1 comprises a body 4 in the shape of a gun on which is pivotally mounted a grip 5 that can be moved by manual force. The grip 5 is mounted opposite from another fixed grip 10 molded in the body 4 of the ancillary device 1.

The body 4 is provided with a first chamber 6 into which extends the grip 5 by means of a curved counter-shaft 7. The travel of the grip 5 is limited by the dimensions of an oblong opening 70 provided in the curved counter-shaft 7. The chamber 6 is horizontally traversed by a traction rod 8, also opening on both sides of the body 4. The chamber 6 has an oblong shape provided with an opening 16 on the upper part of the body.

The chamber 6 houses a traction or activating assembly 12 that is constituted by two opposite plates 13, 14 between which is compressed a spring 15. The traction means 12 and particularly the plates 13 and 14 are traversed by the traction rod 8 while the spring 15 is coaxially wound around the rod to come into contact with each of the plates.

The plates 13 and 14 are positioned perpendicular to the longitudinal axis of the traction rod 8, so that the plate 14 is in contact with the curved counter-shaft 7 of the mobile grip 5. It can also be seen that the plates 13 and 14 protrude to the outside of the body 4 of the ancillary device 1 through the opening 16 of the chamber 6.

The mobile grip 5, actuated manually, causes the curved counter-shaft 7 to move the plate 14 so that it presses against the traction rod 8 due to the compression force of the spring 15, while the other plate 13 remains always perpendicular to the rod and against the vertical wall 17 of the body 4, separating the two chambers 6 and 9.

The body 4 includes a second chamber 9 provided in an extension of the body and on the side of the fixed grip 10. The traction rod 8 traverses the chamber 9 in such a manner that an upper end of the rod interacts with a movable head 11. The chamber 9 has a lower opening 18 that is turned to the side of the fixed grip 10 for the passage of a hinged lever 19. The lever 19 interacts with a blocking catch 20 actuated by a torsional spring 21 that is housed in the fixed grip 10.

The lever 19 is in contact with a plate 22 that is located around the traction rod 8 and in the second chamber 9. The extremity of the plate 22, located opposite from the one interacting with the lever 19, is movable in an aperture 23 provided in the body 4 and opposite the opening 18. The insertion of the plate 22 into the aperture 23 allows a pivoting of the plate when it is subjected to a rocking force generated by the lever 19.

The chamber 9 is affixed to a ferrule 24 that is screwed into a vertical wall 25 opposite to the wall 17 of the body 4. The ferrule 24 is traversed by the traction rod 8 for the positioning of a spring 26 that is wound around the rod and compressed between the ferrule and the plate 22. The ferrule 24 allows the adjustment of the tension of the spring 26.

The above described device mounted in the chamber 9 of the ancillary device constitutes a system of locking and disengagement allowing engagement and retention of the rod or a disengagement allowing a free rotating and translational movement of the traction rod 8 with respect to the body 4.

In fact, the disengaged position of the ancillary device 1 (dotted line in FIG. 1) is obtained by pressing upon the lever 19 until it becomes blocked by the catch 20 pushed by the tensional spring 21. The rocking of the lever 19 allows the displacement of the plate 22 in a vertical direction so that it binds the plate in its aperture 23.

In this disengaged position, the traction rod 8 is attached to the plate 14 which allows, when one presses the mobile grip 5, to move the rod towards the back or rear of the body 4. When one releases the grip 5, the spring 15, compressed between the plates 13 and 14, allows the traction rod to move towards the front of the body to its original position.

The disengaged position of the ancillary device 1 allows the surgeon to introduce the suture anchor 2, 3 into the bone either by screwing it in or by striking the movable head 11 affixed to the end of the traction rod 8. When the suture anchor 2, 3 is introduced into the bone by screwing it in, the head 11 is first removed to allow the surgeon to directly act upon the traction rod 8 to bring it into rotation. The rotary movement of the traction rod 8 can be effected manually by means of a handle or a drill, not illustrated herein, that is attached to the rod.

The engaged or locked position of the ancillary device 1 (solid line in FIG. 1) is obtained by pressing on the catch 20 to release the lever 19 for the plate 22 to press the plate against the traction rod 8 under the force of the spring 15. In this engaged position, the traction rod 8 is no longer free to move either in rotation or in translation with respect to the body 4 of the ancillary device 1. Thus, the traction rod 8 is held firmly against the plate 14 which, when one presses on the mobile grip 5, allows the rod to be moved towards the back of the body 4. When one releases the grip 5, the traction rod 8 remains locked in this position.

The engaged position of the ancillary device 1 allows the surgeon, when the suture anchor 2, 3 has been previously inserted into the bone, to deform the fixation elements of the anchor to fix it into the bone and to shape it to attach the soft tissues to be secured to the bone.

A nose 27 is affixed as an extension of the chamber 6 opposite from the second chamber 9. The nose 27 is traversed by the traction rod 8. Inside the nose 27, around the rod 8, is provided a compression spring 28 that is in contact with the vertical wall of the nose, on the one side, and with a vertical plate 29, on the other side.

The plate 29 is firmly attached to a tube 30 which is movable in translational and within which slides the traction rod 8 when it is subjected to a tractive force. Opposite the plate 29, the tube 30 is firmly attached to a guide 31 provided with an internal threaded section intended for the lodging of either a ferrule 32 or a ferrule 33, allowing the positioning of the suture anchor 2 and 3, respectively.

The plate 29 interacts with an aperture 36 provided in an upper portion of the nose 27, in the proximity of which are etched reference marks 37 that allow monitoring of the force applied to the suture anchor 2, 3 for its deformation.

The nose 27 is affixed to a fixed sleeve 39, mounted coaxially to the tube 30 on which screwed an implement for the deformation of the suture anchor 3 for the fixation of soft tissues to the bone.

The sleeve 39 is constituted by a tube 40, coaxial to the one 30, whose free end, disposed around the ferrule 33 corresponding to the positioning of the suture anchor 3, has a curved edge 41 in order to bend the fixation elements of the suture anchor.

The traction rod 8 is provided at the guide 31 with an end 34 that is of less diameter than the remainder of the rod and that traverses either the ferrule 32 or the ferrule 33 depending on which suture anchor 2, 3 is to be fixed. The section of the end 34 of the traction rod 8 outside of the ferrule 32, 33 includes a threaded section 35 to be screwed into the suture anchor 2, 3.

Figure 4A:
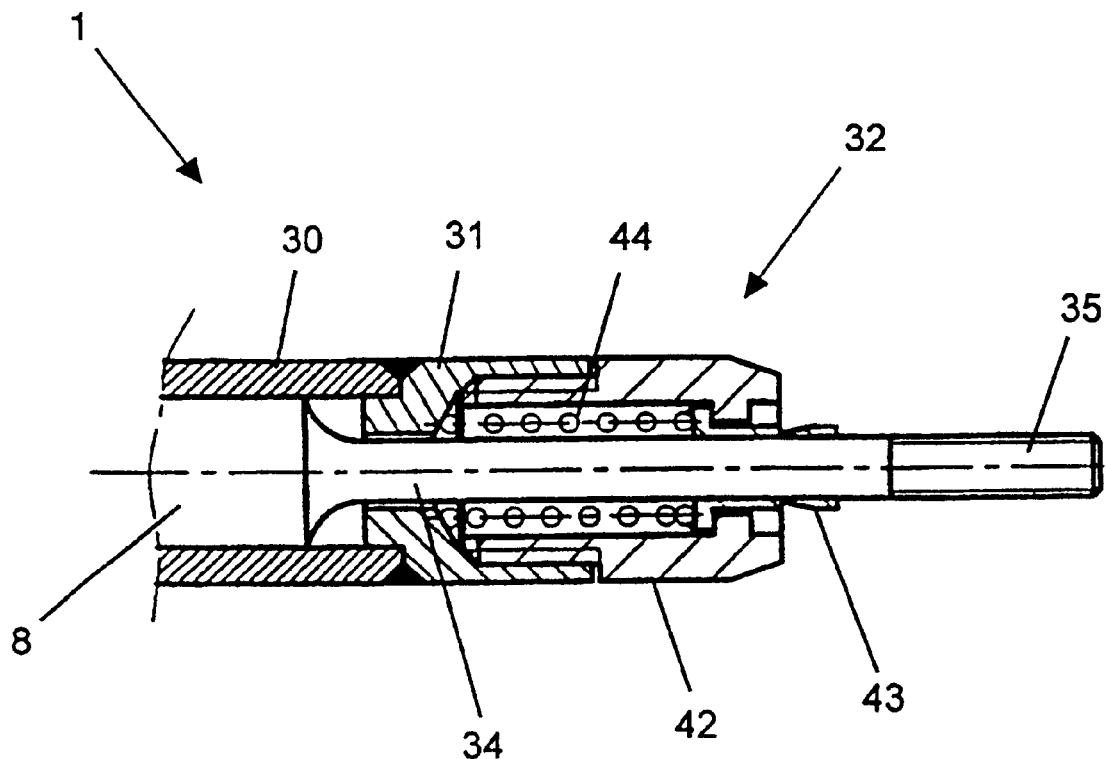
FIGS. 4a and 4b are views illustrating in detail the ferrules to be affixed to the ancillary device in order to adapt the implants.

FIG. 4a illustrates the ferrule 32 for the positioning of the suture anchor 2, that includes a cylindrical body 42 of which one section is screwed into the inside of the guide 31 while another section presses against the suture anchor. The section pressing against the suture anchor is attached in proximity of the traction rod 8 to a thread guide 43. Inside of the body 42 is a spring 44 that presses against thread guide 43 and the inside of the guide 31 is affixed to the tube 30.

Figure 4B:
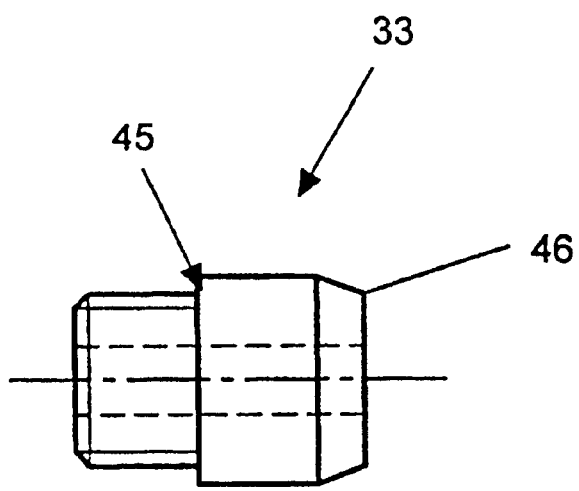

FIG. 4b illustrates the ferrule 33 for the positioning of the suture anchor 3, that includes a cylindrical body 45 of which one section is screwed into the guide 31 while another section has a conical side 46 that presses against the suture anchor 3.

Figure 5A:
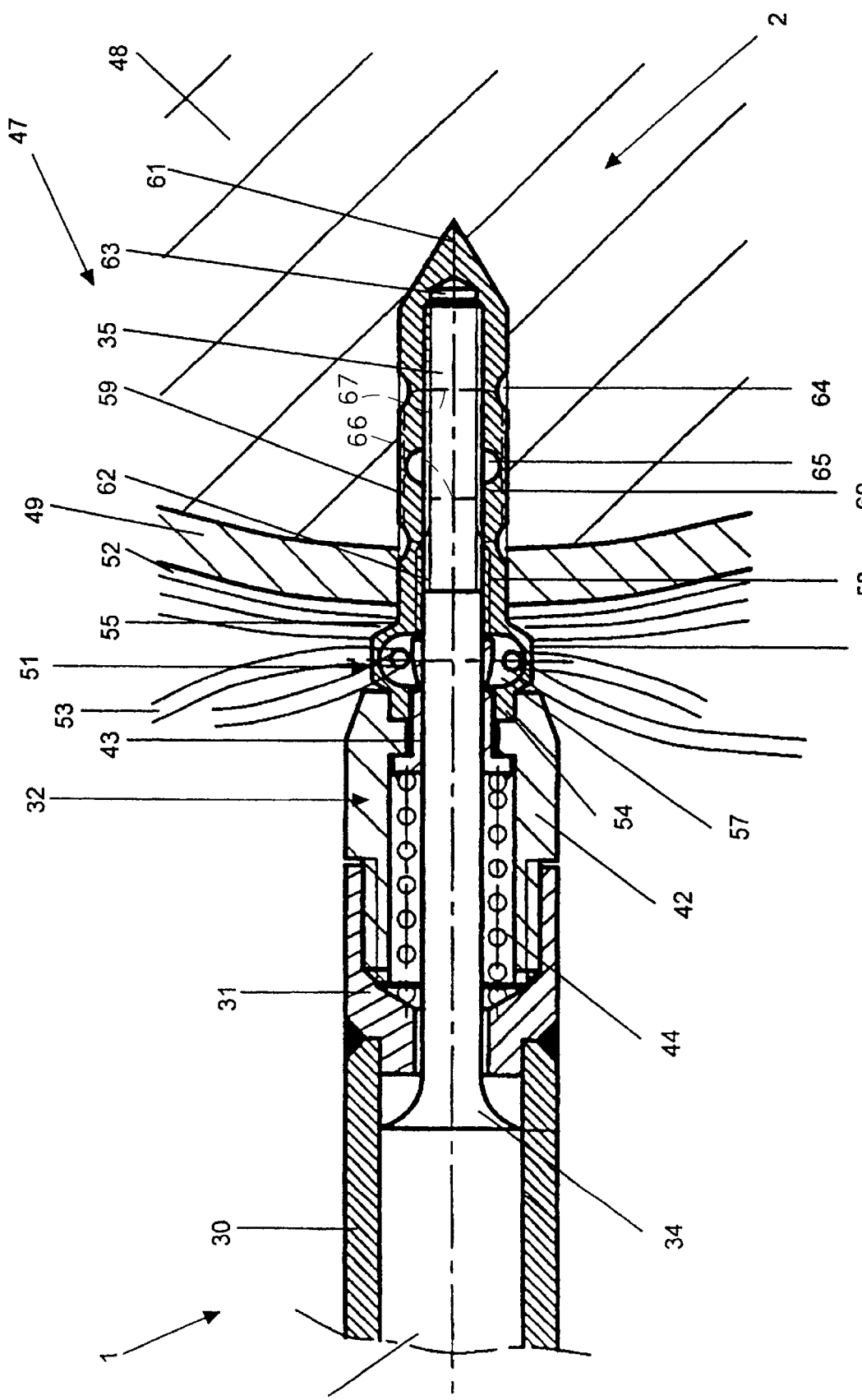
FIGS. 5a to 5c are views illustrating the deformation of an implant by means of the ancillary device according to the present invention for, on the one hand, its fixation into the bone and, on the other hand, the fastening of the suture thread.
Figure 5B:
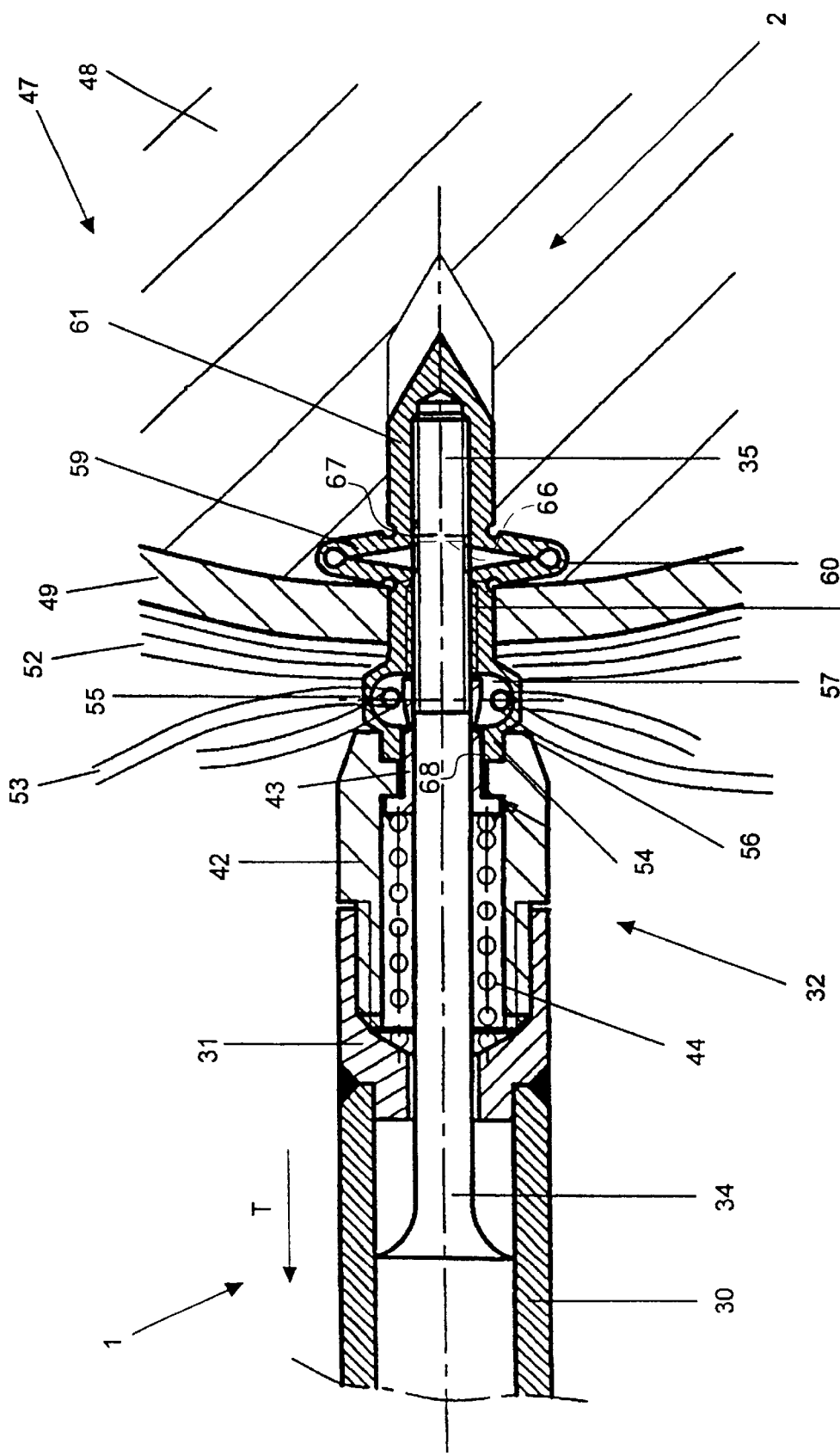
Figure 5C:
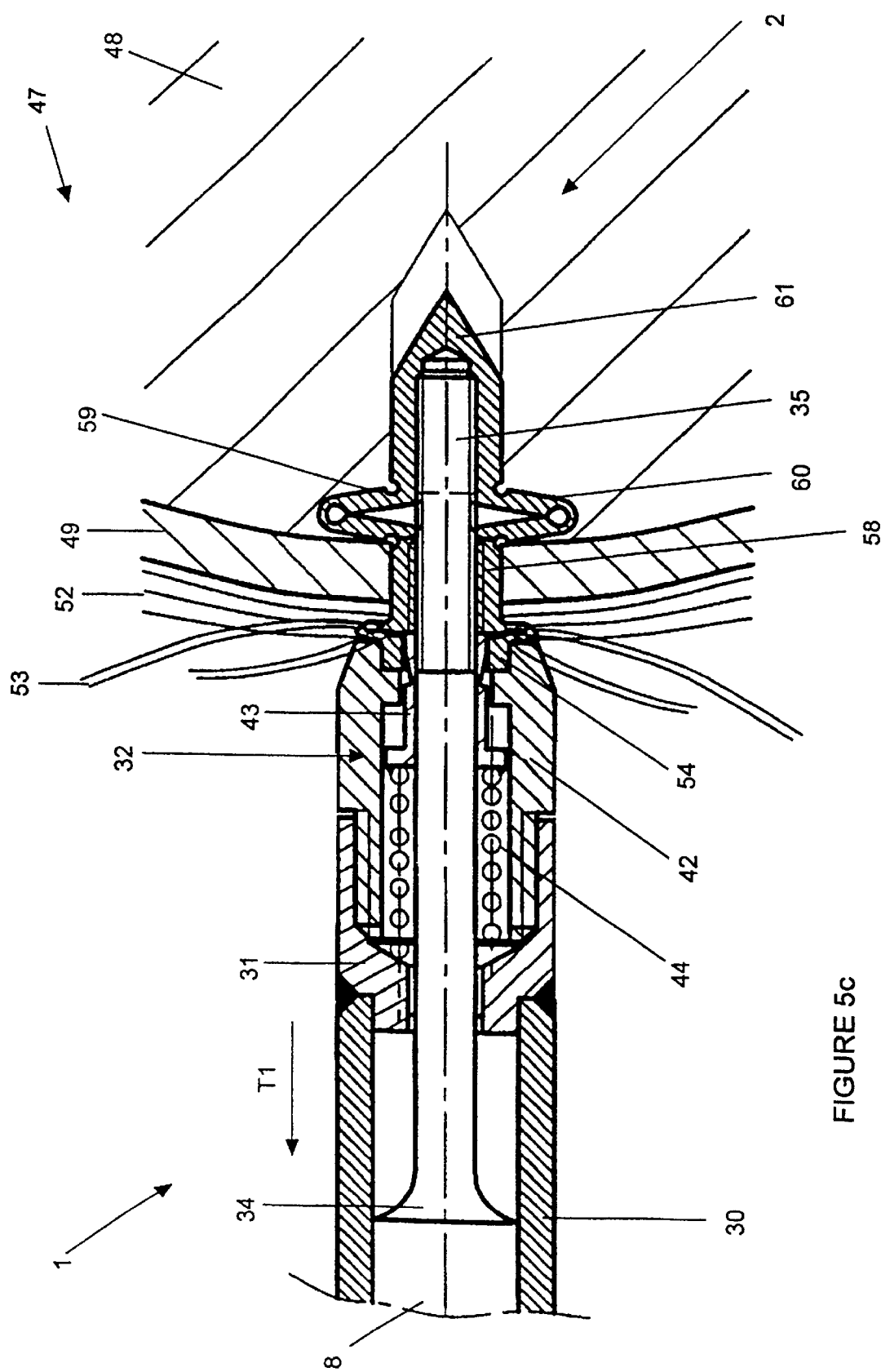

FIGS. 5a to 5c illustrate the positioning of the suture anchor 2 by means of the ancillary device 1 into a patient's bone 47, that consists of the spongy bone 48 and the cortical bone 49. The suture anchor 2 includes an elongated, hollow cylindrical body 50 susceptible to plastically deform and that can be positioned at the surgical location by means of arthroscopy.

The body 50 comprises a head 51 enabling the fixation of soft tissues 52 to the bone of a patient by means of one or several suture threads 53 that are fastened to the head. The head 51 includes a cylindrical support face 54 that extends by means of two tongues 55, 56, opposite and parallel to the longitudinal axis XX' of the body 50, prior to their deformation. The tongues 55 and 56 delimit an oblong clearance 57 that allows the surgeon to pass at least one suture thread 53 therethrough when operating.

The tongues 55 and 56 are connected opposite from the face 54 to a cylindrical section 58 that extends by at least two fixation prongs 59, 60 that, prior to deformation, run parallel to the longitudinal axis XX' of the body 50. The prongs 59 and 60 are extended parallel to the axis XX' by a conical point 61 that facilitates the positioning of the suture anchor in the bone 47. The cylindrical section 58 includes an internal threaded borehole 62 on the axis XX', which bore opens, on the one hand, between the tongues 55, 56 and, on the other hand, between the fixation prongs 59, 60.

The conical point 61 is provided on its inside with a threaded blind hole 63 that opens between the fixation prongs 59, 60 and is bored into the same longitudinal axis XX' as the borehole 62. Further, the diameter of the borehole 62 is greater than that of the threaded hole 63.

The prongs 59 and 60 are attached to the cylindrical section 58 and to the point 61 by bending fasteners 64 in a direction toward the center of the body 50 and that allow the prongs to deform by means of a tensile force applied by the rod 8 of the ancillary device 1.

The prongs 59 and 60 are also provided in their middle with a bending fastener 65, opposite to each other and in reverse direction to constitute two identical segments and of the same length.

Between each prong 59 and 60 is provided a stop 66 affixed to the cylindrical section 50 oriented in direction to the conical point 61. Each stop extends parallel to the longitudinal axis XX' of the body 50 and has a length that depends on the deformation one wishes to obtain from the prongs 59 and 60. In fact, the deformation of the prongs 59 and 60 is limited by the stops 66 that press against a face of the conical point 61. The face 67 is on a plane perpendicular to one bearing the axis XX' of the body 50.

In support face 54, on which meet the tongues 55, 56 opposite from the cylindrical section 58, is drilled a borehole 68, coaxial to the threaded borehole 62 but with greater diameter. The borehole 68 opens between the tongues 55, 56 and inside the oblong clearance 57.

FIG. 5a illustrates, after the positioning of the suture anchor 2 in the bone 47, the traction rod 8 screwed in the blind hole 63 of the conical point 61. Into the guide 21, affixed to the tube 30, is screwed the ferrule 32 in such a manner that the thread guide 43 penetrates through the borehole 68 inside the oblong clearance delimited by the tongues 55, 56 of the anchor 2. In this position, the face 54 of the suture anchor 2 is pressed against the ferrule 32 of the ancillary device and the surgeon may place, in the oblong clearance 57, the suture threads 53.

The surgeon then places the ancillary device 1, by means of the lever 19, in its engaged or locked position so that the traction rod 8 cannot effectuate a translational nor rotational movement.

In FIG. 5b is illustrated the deformation of the suture anchor 2 and, more specifically, the prongs 59 and 60 inside of the spongy bone 48 when a tensile force T is applied to the rod 8. The tensile force T is generated by successive compressions of the mobile grip 5 by the surgeon in order to displace horizontally, by means of the plate 14, the traction rod 8 according to the axis XX' with respect to the body 4. It should be noted that, when the rod 8 is displaced into the body 4, the ferrule 32 is pressed against the face 54 of the suture anchor 2.

The deformation of the prongs 59 and 60 is limited until the conical point 61 presses against the herein not illustrated stops of the body 50. As soon as the face of the conical point 61 comes to press against the stops 66 by means of its face 67. As soon as the face 67 presses against the stops 66, the surgeon releases the grip 5. The force T applied to the suture anchor 2 is controlled by the displacement of the plate 29 with respect to the reference marks 37 etched into the nose 27.

The prongs 59 and 60 deform under the effects of a compression force due to the traction force T applied to the rod 8 of the ancillary device 1 according to the shape of the fasteners 64 and 65, so that segments of the prongs are oriented towards the outside of the body 50 and in a direction essentially perpendicular to the axis XX'.

It is thus noted that the fixation of the suture anchor 2 to the spongy bone 48 is effected by the deformation of the prongs 59 and 60 until one of the segments comes into contact with the internal face of the cortical bone 49.

In FIG. 5c is illustrated the fastening of the suture threads to the head 51 of the anchor 2 through the deformation of the tongues 55, 56.

Bringing the conical point 61 in contact with the stops 66, the surgeon can press anew the grip 5 to apply a tensile force T1, greater than that of T, to the traction rod 8, without risking damage to the prongs 59 and 60, to deform the tongues 55 and 56.

The deformation of the tongues 55 and 56 reduces the oblong clearance 57 in order to block, in a taut position, the suture threads 53 on the head 51 of the suture anchor 2.

At the time of the deformation of the tongues 55, 56, the thread guide 43 allows the suture threads 53 to be removed from the traction rod 8 so as not to damage them. The thread guide 43 is kept in contact with the inside of the suture anchor 2 by the spring 44 that is independent of the operation of the ancillary device 1. The suture threads 53 allow the surgeon to ligature the soft tissues 52 to the suture anchor 2. After the fastening of the suture threads 53, the surgeon disengages the ancillary device 1 and unscrews the traction rod 8 to withdraw it from the suture anchor 2.

Figure 6A:
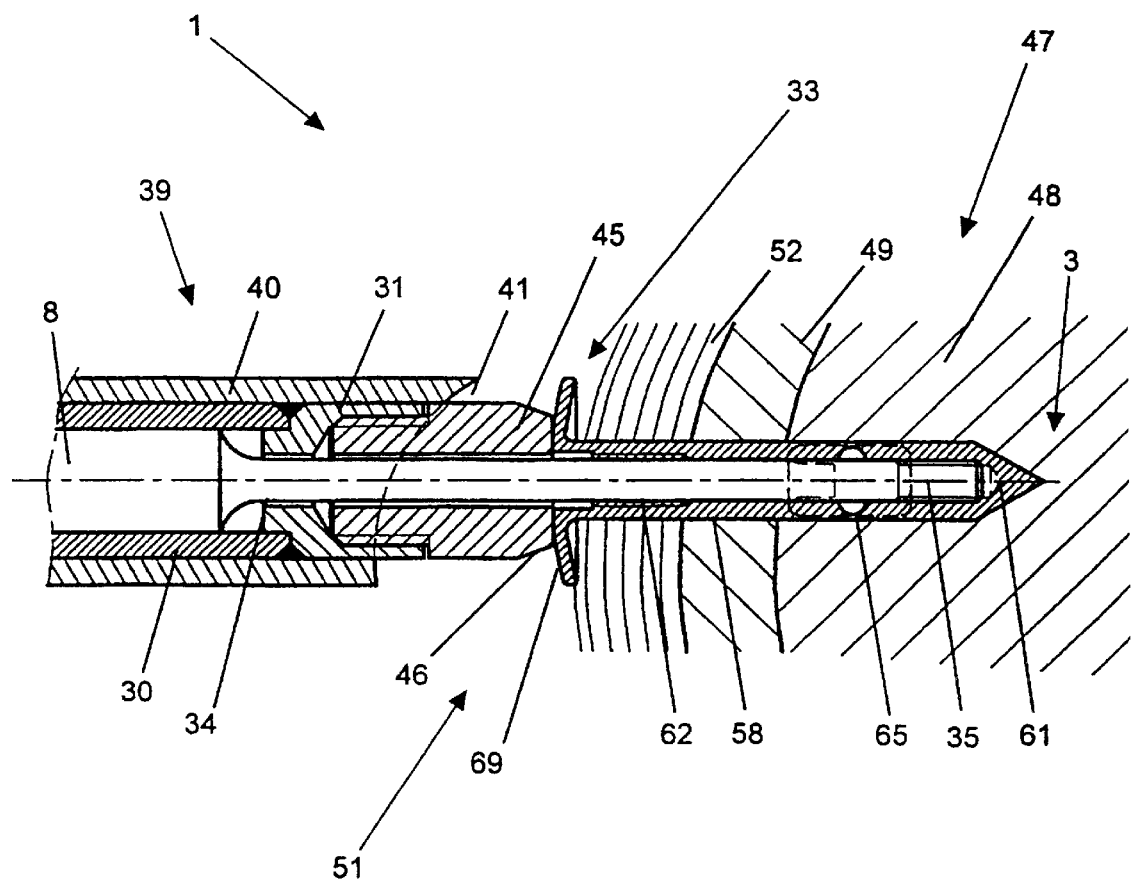
FIGS. 6a to 6c are views illustrating a variant of the ancillary device for the shaping of a head of an implant for the fixation of soft tissues to the bone of a patient.
Figure 6B:
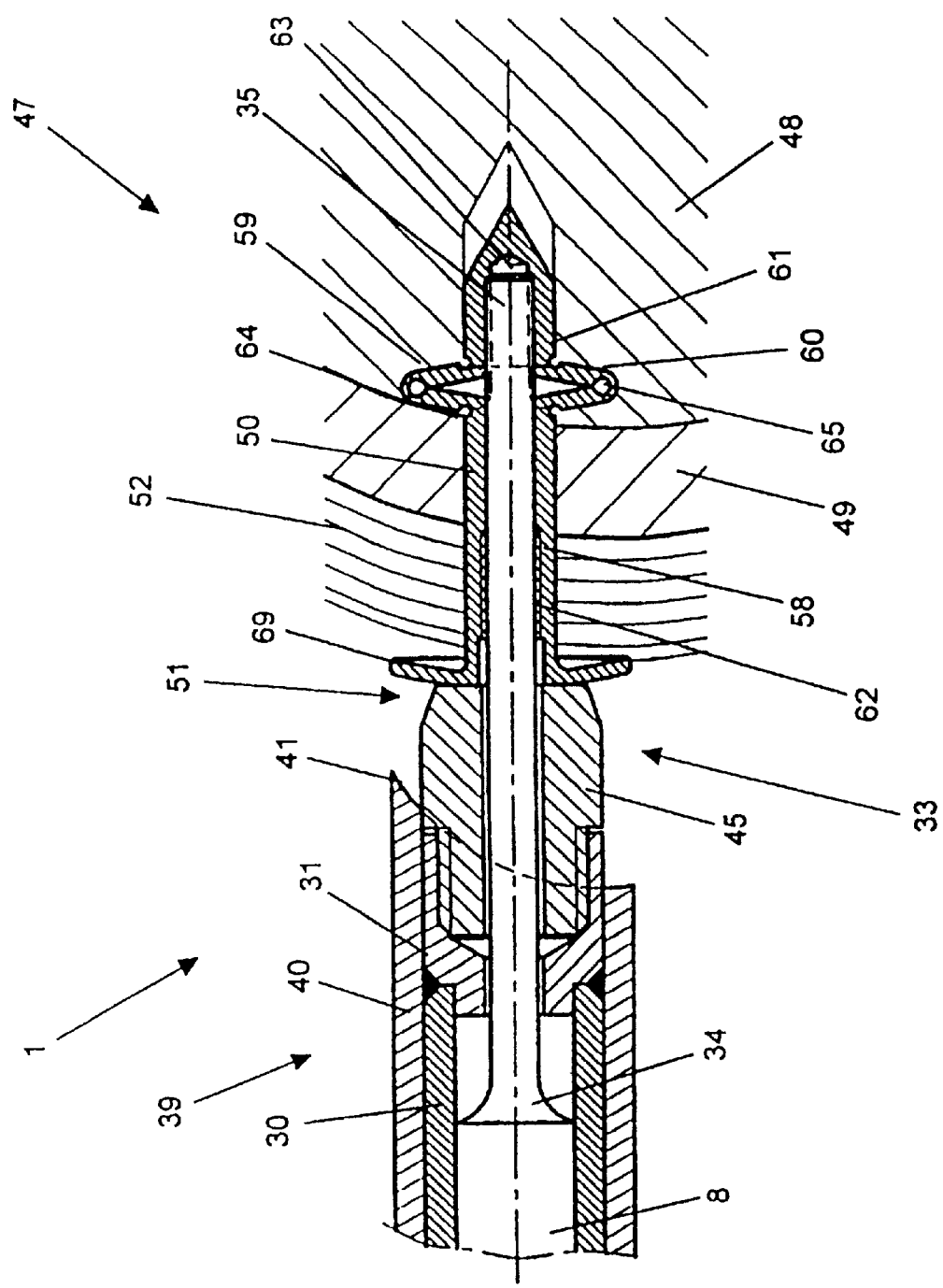
Figure 6C:
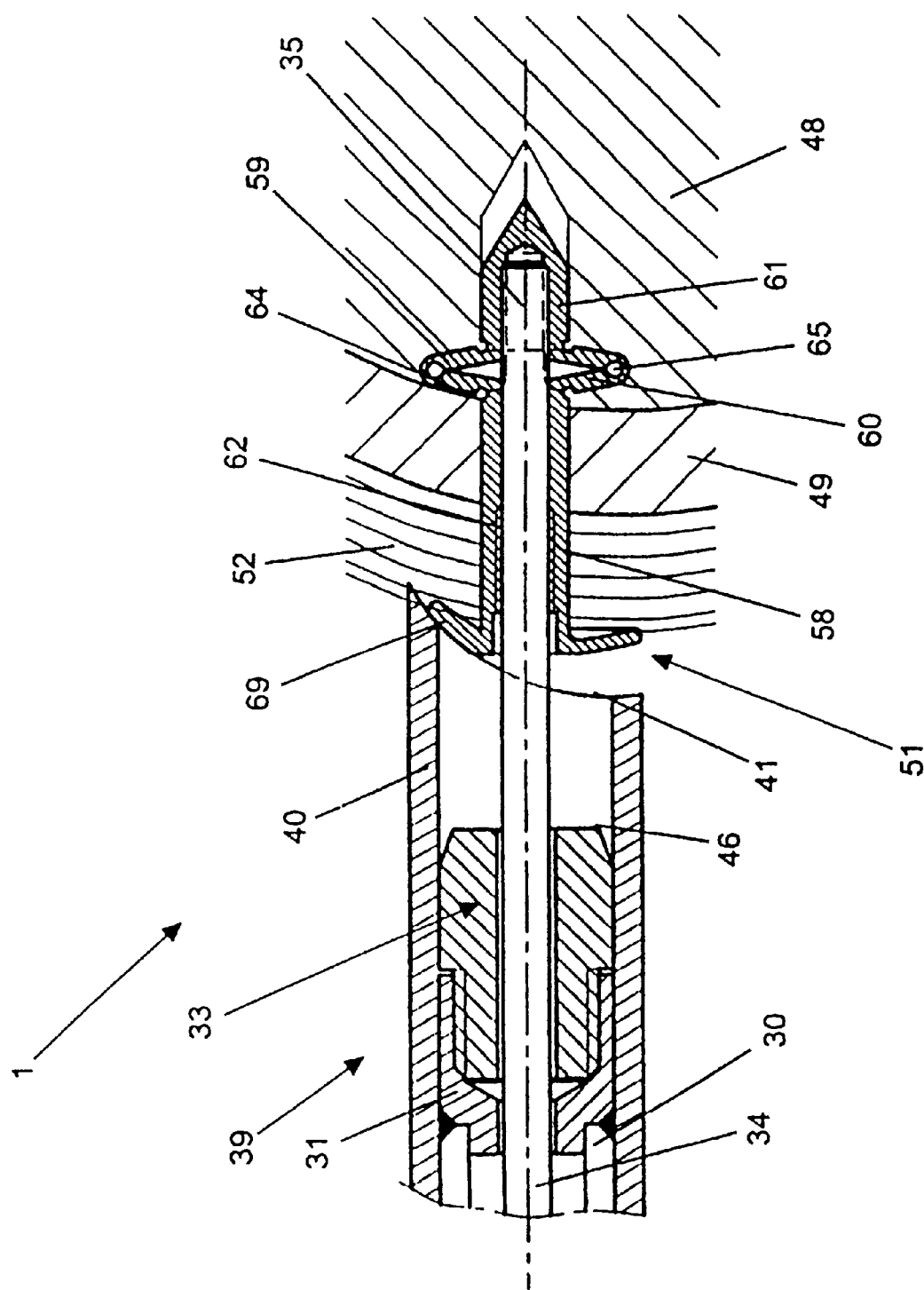

FIGS. 6a to 6c illustrate the positioning of the suture anchor 3 by means of the ancillary device 1 in the bone 47 of a patient, which bone is constituted by the spongy bone 48 and the cortical bone 49.

The suture anchor 3 is similar to the anchor 2 but the head 51 is not provided with the tongues 55 and 56 for the fastening of the suture threads 53. The head 51 includes the cylindrical section 58, longer than the one described above, and into which is drilled the internal threaded borehole 62. This bore opens, on the one hand, between the prongs 59 and 60 and, on the other hand, to the outside of the body 50 by a coaxial borehole 25 of greater diameter. The head 51 is provided at the end of the cylindrical section 58, and opposite from the prongs 59 and 60, with a disk 69 that can be adapted to allow the holding of the soft tissues 52 to the bone 47.

The steps for the insertion and the fixing of the suture anchor 3 into the bone 47 are the same as those described above in FIGS. 5a and 5b for the suture anchor 2. It should be noted that for the positioning of the suture anchor 3 in the bone 47, the ancillary device 1 is provided with a ferrule 33 that is screwed on to the guide 31, and shaping implement 39 is also screwed on to the nose 27.

When the suture anchor 3 is affixed to the bone 47 and, more specifically, to the spongy bone 48, as the prongs 59 and 60 are deformed by means of the traction rod 8 of the ancillary device 1, the surgeon thereafter disengages the rod 8 by pressing on the lever 190 to bring the plate 22 to a vertical position (dotted line in FIG. 1). This disengaged position allows the surgeon to draw back the ancillary device 1 and the ferrule 33 but leaves the traction rod 8 screwed into the suture anchor 3 (FIG. 6c).

The surgeon engages anew the ancillary device 1 by means of the lever 190 to lock the translational and rotational movement of the traction rod 8 with respect to the body 4. The surgeon brings the shaping implement 39 against the disk 69 of the head 51 by unscrewing it slightly from the nose 27 (FIG. 6c). Lastly, the surgeon presses successively the grip 5 in order to subject the shaping implement 39 to a sufficient force for the deformation of the disk 69 in order to fasten the soft tissues against the cortical bone 49.

The shape or the bending of the disk 69 is effectuated in several phases by successive rotations of the implement 39 around its axis to present the curved shape 41 in another position. The surgeon proceeds in the same manner as above to reshape the disk 69.

After the deformation of the disk 69, the surgeon disengages the ancillary device 1 to unscrew the traction rod 8 to withdraw it from the suture anchor 3.

Figure 7:
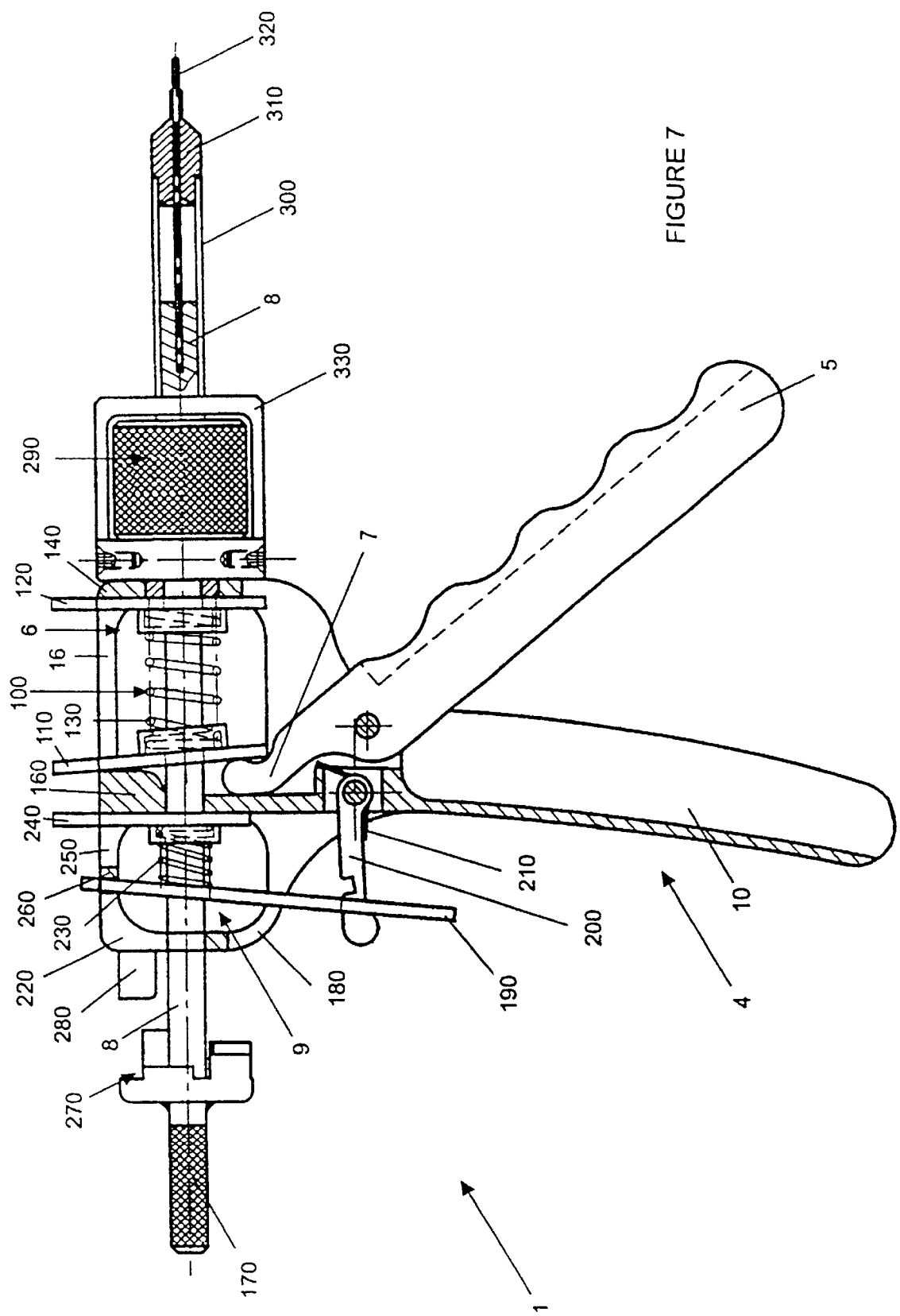
FIG. 7 is a sectional drawing illustrating the ancillary device according to the present invention.
Figure 8:
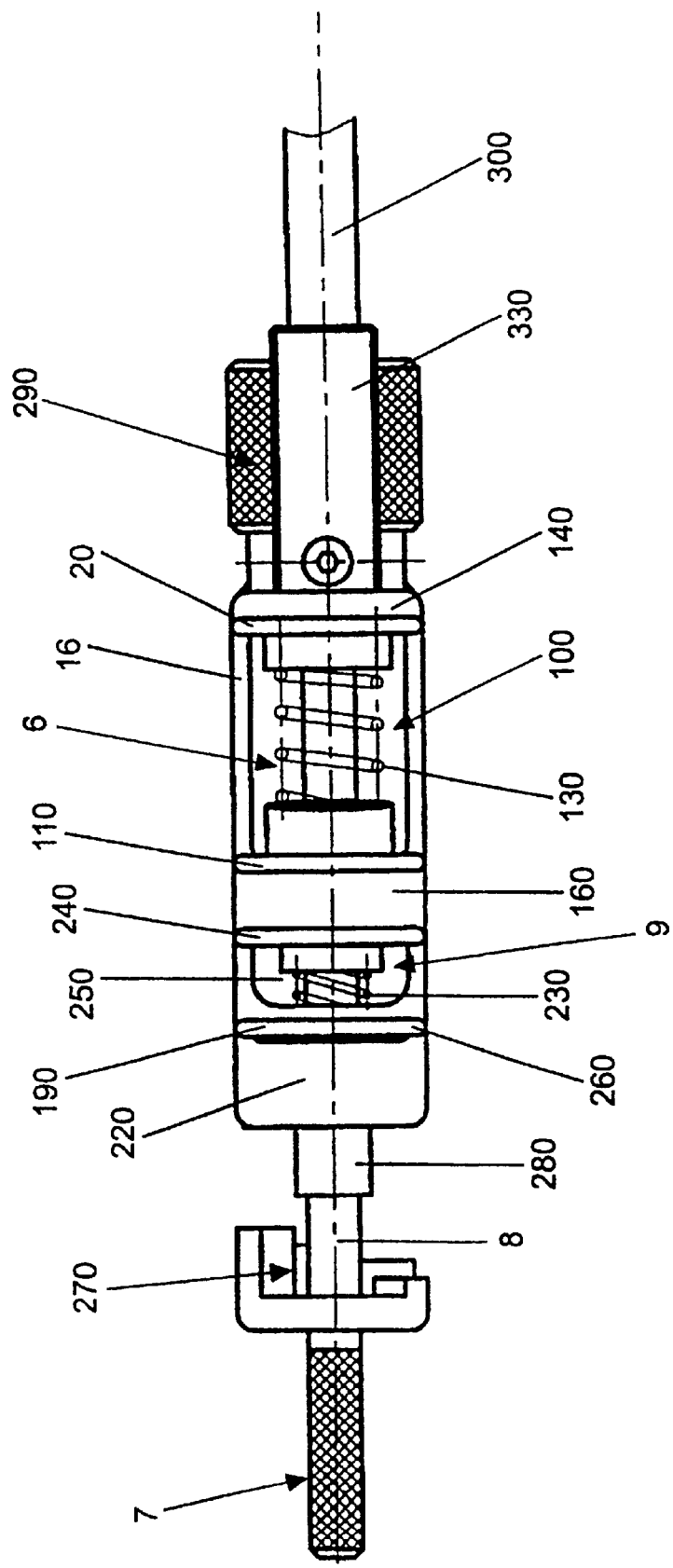
FIG. 8 is a horizontal projection illustrating the ancillary device according to the present invention.
Figure 9:
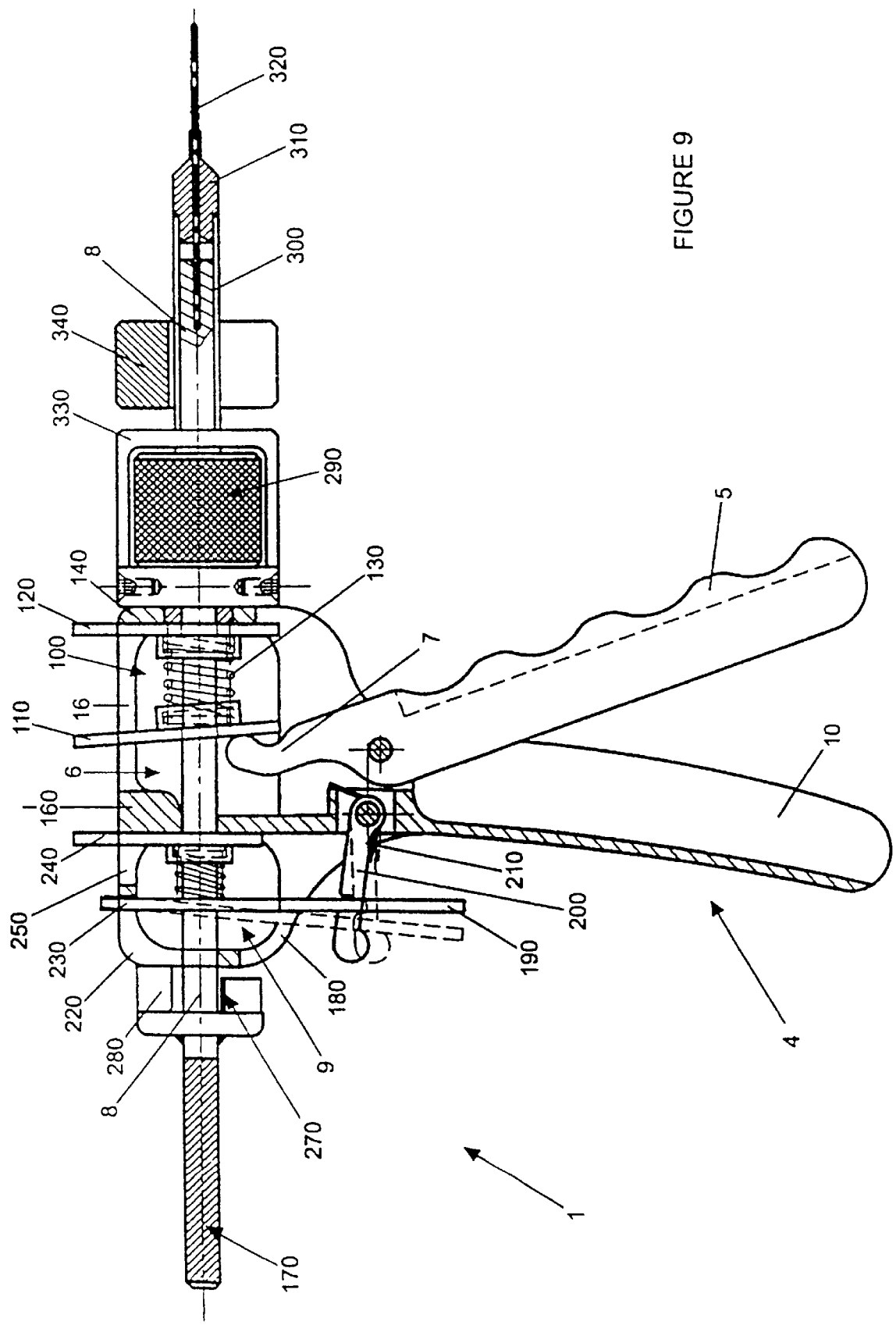
FIG. 9 is a sectional drawing illustrating the ancillary device in a compressed position for the deformation of the implant to be removed from the bone.

FIGS. 7 to 9 illustrate an ancillary device 1 allowing in particular, but not in a limiting manner, the withdrawal of implants, such as suture anchors 2, 3.

The ancillary device 1 allows the withdrawal of the reversible expansion suture anchor 2, 3 from the bone of a patient by a deformation of the fixation means of the anchor, in order to return them to a position essentially identical to their original one.

The body 4 has the shape of a gun on which is hinged the grip 5 that can be manually displaced. The grip 5 is located opposite another fixed grip 10 formed within the body 4 of the ancillary device 1. The body 4 is provided with a first chamber 6 into which opens the grip 5 by way of a curved counter-shaft 7. The chamber 6 is traversed horizontally by a rod 8 that also comes out on both ends of the body 4. The chamber 6 is of oblong shape provided with an aperture 16 on the upper part of the body 4.

The chamber 6 houses the compression or activating means 100 for the rod 8 that are constituted by two opposite plates 110, 120 between which is compressed a spring 130. The compression means 100 and, more specifically, the plates 110 and 120, are traversed by the rod 8, while the spring 130 is coaxially wound around the rod to come into contact with each of the plates. The plates 110 and 120 are affixed to the rod 8 in such a manner that the plate 110 is in contact with the curved end 7 of the mobile grip 5 in an inclined direction with respect to the longitudinal axis of the rod. It should also be noted that the plates 110 and 120 protrude outside the body 4 of the ancillary device 1 through the aperture 16 of the chamber 6.

The mobile grip 5, manually actuated, causes the plate 110 to press against the rod 8 by compressing the spring 130 while the other plate 120 remains perpendicular to the rod and against the vertical wall 140 of the body 4, delimiting the chamber 6.

The body 4 is provided with a second chamber 9 on the extension of the first chamber 6 and on the opposite side of the vertical wall 140. The chamber 9 is separated from chamber 6 by a vertical wall 160 that is located in the extension of the fixed grip 10 of the body 4. The chamber 9 is horizontally traversed by the rod 8 in such a manner that the end of the latter, being outside of the body 4 and behind the fixed grip 10, interacts with a knurled head 170.

The knurled head is provided with notches 270 of different dimensions that interact with a stop 280 on an upper part of the chamber 9 and outside of it, to allow the rod 8 to effect more or less travel or movement depending on the model of the implant or the suture anchor 2, 3 to be withdrawn.

The chamber 9 is provided with an aperture 180 on its underside that is turned to the side of the fixed handle for the passing of a plate member 190. At one of its extremities, the plate member 190 interacts with a blocking catch 200 pushed by a torsional spring 210 that is housed in the fixed grip 10.

The plate 190 is arranged around the rod 8 and in the second chamber 9 in such a manner that the other extremity, opposite from the one interacting with the catch 200, is housed inside an aperture 220 provided in the body 4. By means of a spring 230, wound around the rod 8, the plate 190 is connected to another plate member 240 that presses against the vertical wall 160. The plate member 240 extends into another upper aperture 250 provided in the body 4 of the ancillary device 1. The apertures 220 and 250 are separated by a partition 260 against which abuts the plate 190 in a tilted direction with respect to the longitudinal axis of the rod 8.

The above-described device mounted in the chamber 9 of the ancillary device 1 constitutes a locking and disengaging system allowing the rod 8 to effect or not a rotary and translational movement with respect to the body 4. In fact, the disengaged position of the ancillary device 1 (solid line in FIG. 9) is obtained by pressing against the plate 190 until it engages in the catch 200, pushed by the torsional spring 210. It should be noted that, in this position, the plate 190 is in an essentially vertical position under the effect of the thrust of the spring 230, thus abutting the partition 260 and the plate 190 is blocked by the catch 200.

In this disengaged position, the rod 8 is free to move rotationally and translationally with respect to the body 4, so that it can be handled independently of the ancillary device 1.

The engaged or locked position of the ancillary device 1 (solid line in FIG. 7) is obtained by pressing against the catch 200 to release the plate 190 so that it presses against the rod 8 under the effect of the spring 230. In this engaged position, the rod 8 is no longer free to move either in rotation or translation with respect to the body 4 of the ancillary device 1. Thus, the rod 8 remains secured to the plate 110 which, when pressing the mobile grip 5, allows the rod to move towards the front of the body 4. When one releases the grip 5, the rod 8 remains blocked in this position.

The engaged position allows the surgeon to withdraw the suture anchor 2, 3 by applying a sufficiently strong force to deform the fixation elements of the anchor, so that they return to a position essentially equivalent to their original one.

In the extension of the chamber 6 and opposite from the chamber 9, a knurled element 290 is affixed to the body 4, to which element is affixed a sleeve 300 in which slides the rod 8. To the free end of sleeve 300 is affixed a threaded ferrule 310 that is longitudinally traversed by a chambered section 320 constituting a thruster for the rod 8. The knurled element 290 is partially shielded by a housing 330 that is affixed to the body 4 on the extension of the chamber 6.

It can also be noted that a mobile head 340 is adapted to the outside of the sleeve 300 to enable the surgeon to withdraw the suture anchor 2 by knocking against the housing 330.

Figure 10A:
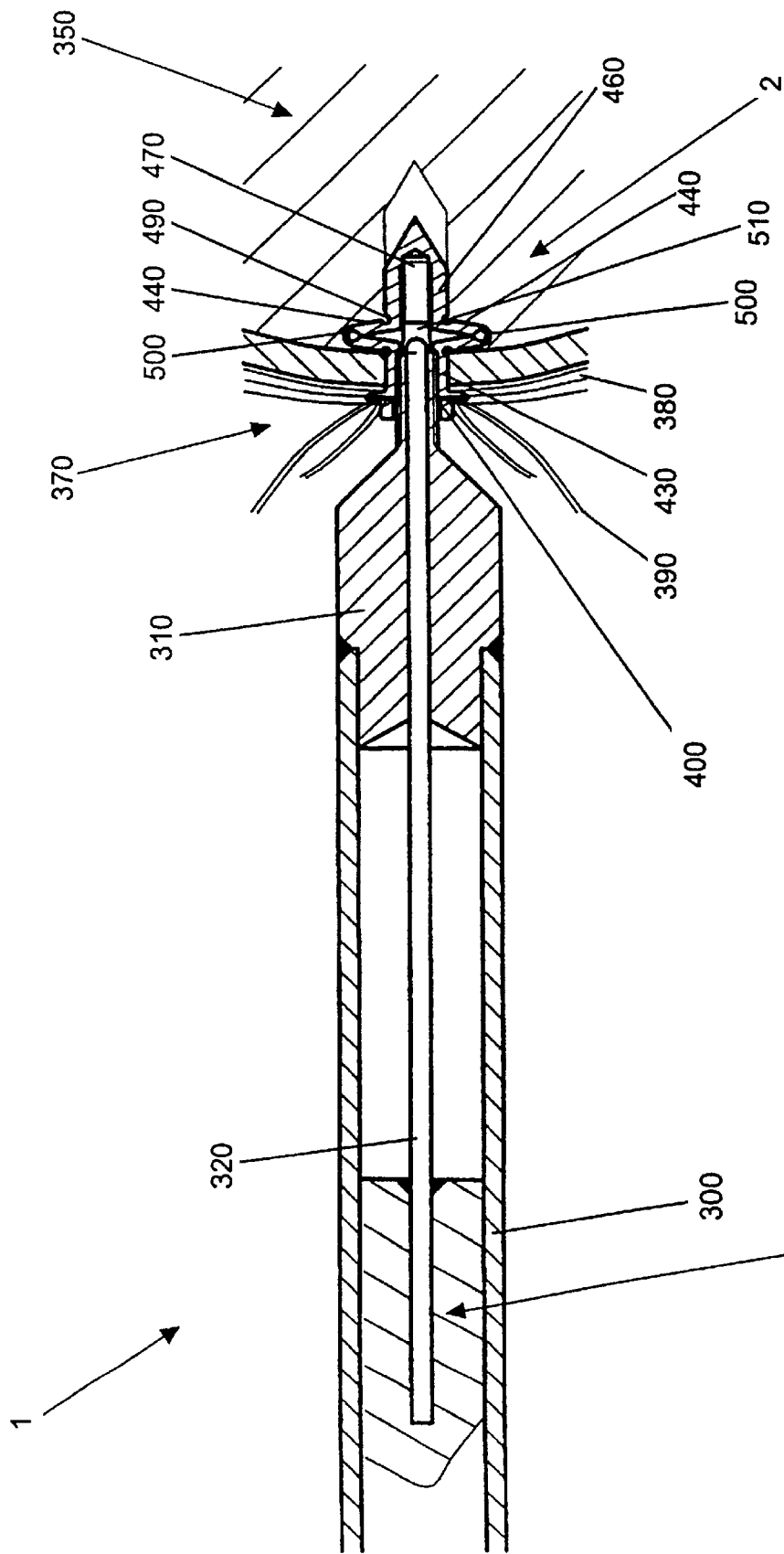
FIGS. 10a to 10c are views illustrating in detail the stages for the removal of the implant by means of the ancillary device according to the present invention.
Figure 10B:
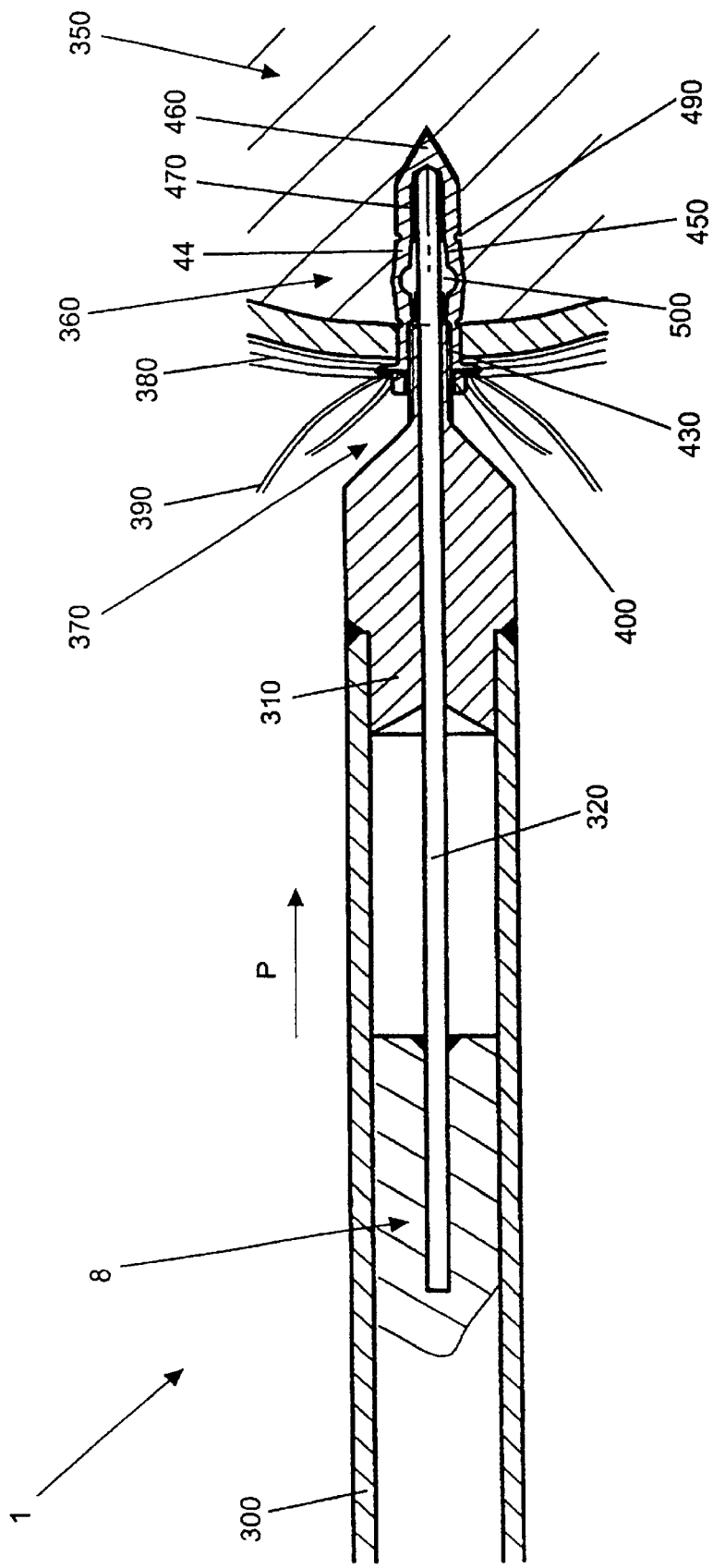
Figure 10C:
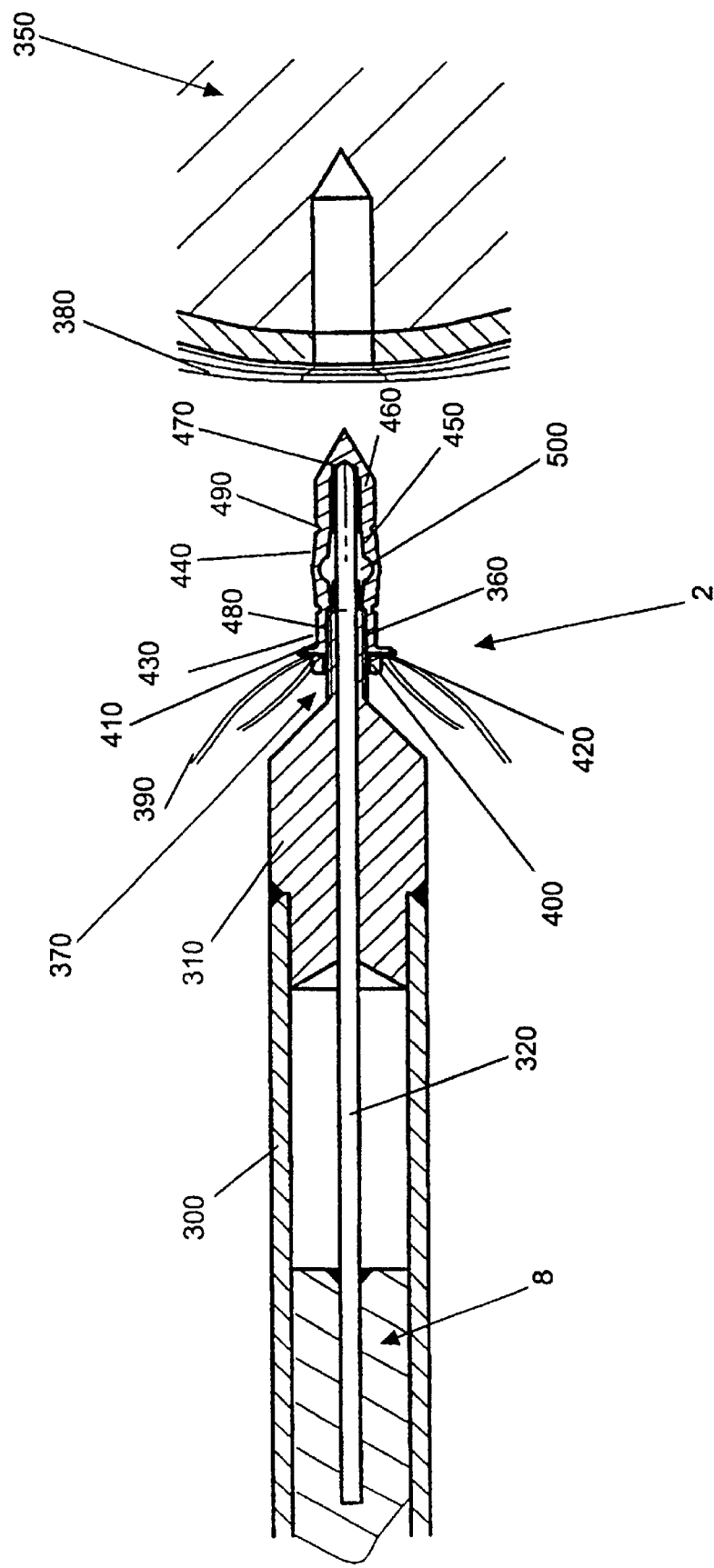

In FIGS. 10a to 10c are illustrated the various steps to use the ancillary device to withdraw the suture anchor 2 from the bone 47, that has been previously described. It allows the withdrawal of the suture anchor assembly having reversible fixation means.

In FIG. 10a is illustrated the insertion of the ancillary device 1 on the surgical location by arthroscopy. Prior to the positioning of the ancillary device 1, the surgeon checks the model of the suture anchor 2 to be withdrawn in order to be able to index, by rotating the rod 8, the notch 270 corresponding to the knurled head 170 so that it is opposite the stop 280 of the body 4. The adjustment of the notch 270 limits the travel of the rod 8 in order to prevent that the suture anchor to be withdrawn without breaking inside of the bone.

Then, the surgeon screws the ferrule 310 of the ancillary device 1 into a disengaged locked position by means of the knurled element 290 inside of the suture anchor 2 and, more specifically, in the threaded borehole 62. The surgeon brings the thruster 320 of the rod 8 to the bottom of the blind hole 63 provided in the conical point 61.

In FIG. 10b the surgeon engages the ancillary device 1 by means of the plate 190 to be able to act upon the rod 8 by pressing the mobile grip 5. The rod 8, through its thruster 320, applies a thrust force P on the conical point 61 in order to swing open the prongs 59, 60 and to bring them into a position essentially parallel to the axis XX' of the body 50 of the suture anchor 2. When the suture anchor 2 has returned to an essentially elongated position, by means of the head 340, the surgeon can strike gently on the sleeve 330 of the ancillary device 1 in order to withdraw the anchor from the bone 47 (FIG. 10c).

The ancillary device 1 allows the withdrawal of the suture anchor 2, or analogous ones, without having to drill a hole whose diameter would be almost that of the hole required for the deformed prongs 59, 60.

It can be noted that for the withdrawal, the ancillary device 1 allows the withdrawal of the suture anchors 2 as well as 3, illustrated and described above for the positioning ancillary device.

What is claimed is:

1. A device for implanting or removing a deformable anchoring implant in a bone of a patient, the device including a body having a front portion and a rear portion, a rod mounted within said body and having a forward end portion extending from said front portion of said body and adapted to engage with the anchoring implant and a rear portion, a movable grip assembly pivotally mounted to said body for selectively operatively engaging an activating assembly for operatively moving said rod in translation relative to said body, and a rod locking and release assembly mounted to said body and movable from a first engaged position wherein said rod is engaged to prevent movement thereof to a second disengaged position wherein said rod is free to move in rotation relative to said body or in translation relative to said body when said movable grip assembly operatively engages said activating assembly for moving said rod in translation.

2. The device of claim 1, including control means for limiting a tensile force (T) applied to said rod for deforming the anchoring implant.

3. The device of claim 1, wherein said control means include a nose (27) affixed to said body in which is provided a compression spring (28) disposed around said rod, and a plate (29) secured to a tube (30) which is free in translational movement and in which said rod is slideably received.

4. The device of claim 3, wherein said plate (29) opens into an aperture (36) in an upper section of said nose (27) and in the proximity of which are reference marks (37) for controlling force applied to the anchoring implant.

5. The device of claim 3, wherein said tube (30) is provided at a free end thereof with a guide (31) with an internal threaded section which is adapted to retain a ferrule (32, 33) adapted to deform the anchoring implant.

6. The device of claim 5, wherein said ferrule (32) includes a cylindrical body (42) of which one section is adapted to be screwed into the guide (31) while another section thereof is adapted to press against the anchoring implant.

7. The device of claim 6, wherein said ferrule (32) is provided on an inside thereof with a spring (44) that is adapted to provide a compression force on a thread guide (43) associated with said ferrule (32).

8. The device of claim 5, wherein said ferrule (32) includes a cylindrical body (42) of which one section interacts with said guide (31) and another section thereof includes a conical face (46) that is adapted to press against the anchoring implant.

9. The device of claim 5, wherein said ferrule (32) is traversed by said rod, said forward end portion of said rod having an extremity (34) which is adapted to be screwed into the anchoring implant.

10. The device of claim 3, wherein said nose (27) supports a shaping implement (39) oriented coaxial to said tube (30) and adapted to shape the anchoring implant.

11. The device of claim 10, wherein said shaping implement (39) includes a curved forward portion (41).

12. The device of claim 11, wherein said body comprises a first chamber (6) in which are housed said activating assembly, and a second chamber (9) that houses said rod locking and release assembly.

13. The device of claim 1, wherein said body includes a first chamber (6) in which is housed said activating assembly, said activating assembly including traction means (7, 14, 15) and a second chamber (9) that houses elements of said rod locking and release assembly.

14. The device of claim 1, wherein said activating assembly includes first and second plates (13, 14) between which is a compressed spring (15), said second plate (14) interacts with a curved counter-shaft (7) actuated by said movable grip assembly to press said second plate (14) against said rod in order to make it move toward said rear portion of said body.

15. The device of claim 1, wherein said rod locking and release assembly includes a lever (19) that is selectively blocked by an elastically loaded catch (20) on a fixed grip (10) of the body, a plate (22) mounted about said rod within said body, a spring (26) engaging said plate (22), adjustment means for adjusting a force applied to said rod by said plate (22), said plate (22) being movable from said first engaged position wherein said plate (22) engages said rod to said second disengaged position by being pivoted to a position substantially perpendicular to an elongated axis of said rod by force applied to said plate (22) by said lever (19).

16. The device of claim 11, including a head (11) removably mounted to said rear portion of said rod, and said forward portion of said rod having a threaded section (35) that is adapted to be screwed into the anchoring implant.

17. The device of claim 1, wherein said body is provided with a first chamber (6) in which are housed said activating assembly and a second chamber (9) that houses said rod locking and release assembly.

18. The device of claim 17, wherein said activating assembly includes first and second plates (120, 110) between which is compressed a spring (130), said second plate (110) being movable by said movable grip assembly to press against said rod in order to advance said rod relative to said front portion of said body.

19. The device of claim 18, wherein said rod locking or release assembly includes a first plate member (190) which is selectively immobilized by an elastically loaded catch (200) provided on a fixed grip (10) of the body, said plate (190) being pressed against said rod by means of a spring (230) associated with a second plate member (240) traversed by said rod, and said first member plate (190) being movable from a vertical position in which such first member plate (190) disengages said rod to a tilted position wherein said first member plate (190) engages said rod.

20. The device in accordance with claim 19, including a knurled element (290) fixed to a sleeve (300) mounted to said front portion of said body and provided at a free extremity thereof with a threaded ferrule (310) that is designed to be screwed into the anchoring implant.

21. The device of claim 20, wherein said knurled element (290) is partially shielded by a housing (330) fixed to said body.

22. The device of claim 20, wherein said rod is provided with a section (320) constituting a thruster that slides inside of the threaded ferrule (310).

23. The device of claim 17, wherein said rod traverses said body from said front portion through said rear portion so as to extend outside of said second chamber (9).

24. The device of claim 1, wherein said rod comprises a knurled head (170) provided with notches (270) of different dimensions, of which after an adjustment of rotation of said rod, at least one of said notches comes into contact with a stop (280) fixed to said body.

* * * * *